US008903680B2

(12) United States Patent
Linn et al.

(10) Patent No.: US 8,903,680 B2
(45) Date of Patent: Dec. 2, 2014

(54) APPARATUS AND METHOD FOR EVALUATING LAYERS IN A MULTI-LAYER STRUCTURE

(75) Inventors: John R. Linn, Maple Valley, WA (US); Jeffrey G. Thompson, Kent, WA (US)

(73) Assignee: The Boeing Company, Chicago, IL (US)

( * ) Notice: Subject to any disclaimer, the term of this patent is extended or adjusted under 35 U.S.C. 154(b) by 491 days.

(21) Appl. No.: 12/965,356

(22) Filed: Dec. 10, 2010

(65) Prior Publication Data
US 2012/0150466 A1    Jun. 14, 2012

(51) Int. Cl.
*G01B 7/02*    (2006.01)
*G01B 7/14*    (2006.01)
*G01N 27/90*    (2006.01)
*G01N 29/265*    (2006.01)
*G01B 7/06*    (2006.01)

(52) U.S. Cl.
CPC ............... *G01B 7/14* (2013.01); *G01N 27/902* (2013.01); *G01N 29/265* (2013.01); *G01B 7/105* (2013.01); *G01B 7/06* (2013.01); *G01B 7/107* (2013.01)
USPC ................ 702/170; 702/38; 702/65; 702/97; 702/127

(58) Field of Classification Search
CPC ............ G01B 7/14; G01B 7/105; G01B 7/06; G01B 7/107; G01N 27/902; G01N 29/265
USPC ........... 702/38, 65, 83, 94, 97, 113, 115, 127, 702/155, 162, 170, 172
See application file for complete search history.

(56) References Cited

U.S. PATENT DOCUMENTS

| | | | | |
|---|---|---|---|---|
| 3,693,075 A | * | 9/1972 | Forster | 324/229 |
| 4,464,332 A | | 8/1984 | Boisseuil et al. | |
| 4,704,801 A | * | 11/1987 | Frizot et al. | 33/502 |
| 4,816,207 A | | 3/1989 | Scharpenberg | |
| 4,876,506 A | * | 10/1989 | Brown et al. | 324/220 |
| 5,124,641 A | * | 6/1992 | Netter et al. | 324/230 |
| 5,128,097 A | * | 7/1992 | Fukasawa et al. | 376/438 |
| 5,341,678 A | * | 8/1994 | Kervinen | 73/150 R |
| 5,371,462 A | * | 12/1994 | Hedengren et al. | 324/225 |

(Continued)

FOREIGN PATENT DOCUMENTS

EP    147037 A3    3/1985

OTHER PUBLICATIONS

UK Intellectual Property Office Combined Search and Examination Report under Sections 17 and 18(3) of Apr. 10, 2012.

*Primary Examiner* — Sujoy Kundu
*Assistant Examiner* — Paul D Lee
(74) *Attorney, Agent, or Firm* — Armstrong Teasdale LLP

(57) ABSTRACT

An apparatus for evaluating layers, including interlayer gaps, in a multi-layer structure; the multi-layer structure presenting a plurality of edges generally aligned athwart an axis; the apparatus includes: (a) a sensing unit configured for sensing at least one parameter; (b) a positioning unit coupled with the sensing unit; the positioning unit being configured to effect moving the sensing unit generally along the axis; and (c) a control unit coupled with at least one of the positioning unit and the sensing unit. The control unit provides an electrical signal to the sensing unit. The control unit monitors changes in the at least one parameter as the sensing unit moves past the plurality of edges. The control unit employs the changes in the at least one parameter to effect the evaluating.

17 Claims, 3 Drawing Sheets

(56) References Cited

U.S. PATENT DOCUMENTS

| | | | | |
|---|---|---|---|---|
| 5,451,872 A | * | 9/1995 | Antonine et al. | 324/262 |
| 5,744,952 A | * | 4/1998 | Latham et al. | 324/207.16 |
| 2007/0023148 A1 | * | 2/2007 | Takagi et al. | 156/578 |

* cited by examiner

APPARATUS AND METHOD FOR EVALUATING LAYERS IN A MULTI-LAYER STRUCTURE

TECHNICAL FIELD

The present invention is directed to material testing apparatuses and methods, and especially to apparatuses and methods for evaluating layers, including interlayer gaps, in a multi-layer structure.

BACKGROUND

In evaluating multi-layer materials one may need to know information relating to layers of the structure, including the sizes of any gaps between layers of the structure. By way of example and not by way of limitation, one may need to know the size of a gap to analyze whether excessive stress exists between layers. Measuring or evaluating layers in a multi-layer structure may be carried out at an edge of the multi-layer structure at which edges of the various layers may be presented. Alternatively, edge evaluation or measurement may be carried out within an aperture that traverses the structure or traverses at least some layers of the structure. Such an aperture may be created for the express purpose of service as a test aperture, or an existing fastener aperture may be employed for measuring or evaluating.

Measurement or other evaluation of layers in a multi-layer structure is not easily carried out if one does not know the thicknesses of various layers in the structure. Access to a free edge of the multi-layer structure may render the evaluating or measuring process easier.

However, in situations in which one is not aware to a certainty of the various thicknesses of layers in a multi-layer structure and especially where no free edge of the structure is presented, there is a need for an apparatus, system and method for measuring or otherwise evaluating layers of a multi-layer structure.

There is a need for an apparatus, system and method for evaluating interlayer gaps in a multi-layer structure.

SUMMARY

An apparatus for evaluating layers, including interlayer gaps, in a multi-layer structure; the multi-layer structure presenting a plurality of edges generally aligned athwart an axis; the apparatus includes: (a) a sensing unit configured for sensing at least one parameter; (b) a positioning unit coupled with the sensing unit; the positioning unit being configured to effect moving the sensing unit generally along the axis; and (c) a control unit coupled with at least one of the positioning unit and the sensing unit. The control unit provides an electrical signal to the sensing unit. In an alternate configuration, the control unit may provide an electrical signal to the sensing unit during the moving. The control unit monitors changes in the at least one parameter as the sensing unit moves past the plurality of edges. The control unit employs the changes in the at least one parameter to effect the evaluating.

A system for determining thicknesses of differing material layers generally along an axis in a multi-layer structure; the thicknesses being bound by a plurality of edges substantially in register crossingly arranged with respect to the axis. For purposes of this disclosure the term "crossingly" may be taken to mean that the edges are not coincident with or parallel with the axis. The system includes: (a) an electromagnetic sensor unit configured for sensing at least one electromagnetic parameter; (b) a positioning unit coupled with the sensor unit; the positioning unit effecting movement of the sensor unit generally along the axis; and (c) a monitoring unit coupled with at least one of the sensor unit and the positioning unit. The monitoring unit provides an electrical input signal to the sensor unit and receives indications of changes in the at least one electromagnetic parameter from the sensor unit as the sensor unit moves along the axis past the plurality of edges. The monitoring unit employs the changes in the at least one electromagnetic parameter to effect the determining.

A method for evaluating layers, including interlayer gaps, in a multi-layer structure to generate a map representing the evaluating; the multi-layer structure presenting a plurality of edges generally aligned athwart an axis; the method including: (a) in no particular order: (1) providing a sensing unit configured for sensing at least one parameter; (2) providing a positioning unit coupled with the sensing unit; the positioning unit being configured to effect moving the sensing unit generally parallel with the axis; and (3) providing a control unit coupled with at least one of the positioning unit and the sensing unit; (b) operating the control unit to provide an electrical signal to the sensing unit during the moving; (c) operating the control unit to monitor changes in the at least one parameter as the sensing unit moves past the plurality of edges; (d) operating the control unit to employ the changes in the at least one parameter to effect the evaluating; and (e) employing the evaluating to generate the map.

It is, therefore, a feature of the present disclosure to provide an apparatus, system and method for measuring or otherwise evaluating layers of a multi-layer structure.

It is another feature of the present disclosure to provide an apparatus, system and method for evaluating interlayer gaps in a multi-layer structure.

Further objects and features of the present disclosure will be apparent from the following specification and claims when considered in connection with the accompanying drawings, in which like elements are labeled using like reference numerals in the various figures, illustrating the preferred embodiments of the disclosure.

DETAILED DESCRIPTION

The terms "coupled" and "connected", along with their derivatives, may be used herein. It should be understood that these terms are not intended as synonyms for each other. Rather, in particular embodiments, "connected" may be used to indicate that two or more elements are in direct physical or electrical contact with each other. "Coupled" may be used to indicated that two or more elements are in either direct or indirect (with other intervening elements between them) physical or electrical contact with each other, or that the two or more elements co-operate or interact with each other (e.g. as in a cause and effect relationship).

Figure 1:
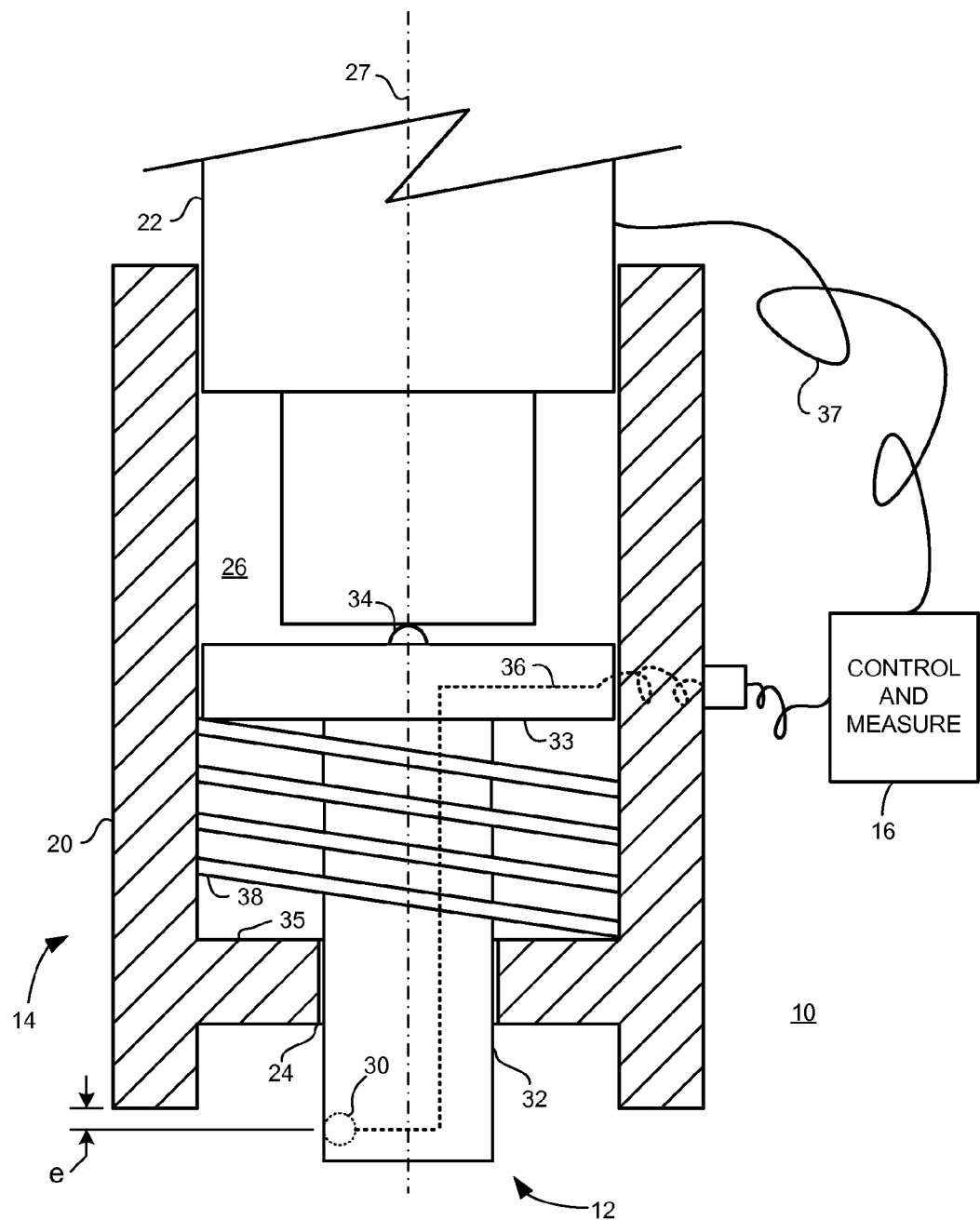
FIG. 1 is a partial section plan view of an exemplary apparatus and system for evaluating layers of a multi-layer structure according to the teachings of the present disclosure.

FIG. 1 is a partial section plan view of an exemplary apparatus and system for evaluating layers of a multi-layer structure according to the teachings of the present disclosure. As used herein, the term "exemplary" indicates an example and not necessarily an ideal. In FIG. 1, an apparatus 10 for evaluating interlayer gaps in a multi-layer structure may include a sensing unit 12, a positioning unit 14 and a control unit 16.

Positioning unit 14 may include a positioning frame 20 (shown in section in FIG. 1) and a moving unit 22. Positioning frame 20 may present an aperture 24 communicating with a well 26. Aperture 24 and well 26 may be substantially symmetrically oriented about an axis 27.

Sensing unit 12 may include a sensor unit 30 mounted with a sensor carrier 32. Sensor carrier 32 may be slidingly received within aperture 24 and bear against moving unit 22. A bearing element 34 may provide substantially all contact between moving unit 22 and sensor carrier 32. By way of example and not by way of limitation, bearing element 34 may be embodied in a ball bearing nestingly engaged with one of moving unit 22 and sensor carrier 32 or bearing element 34 may be embodied in an integrally formed protuberance extending from one of moving unit 22 and sensor carrier 32. Sensor unit 30 may be coupled with control unit 16 such as, by way of example and not by way of limitation, via an electrical connecting conductor 36. Control unit 16 may also be coupled with moving unit 22 such as, by way of example and not by way of limitation, via an electrical connecting conductor 37. Control unit 16 may provide an electrical signal to sensor unit 30. In an alternate configuration, control unit 16 may provide an electrical signal to sensor unit 30 during a moving of moving unit 22. The electrical signal may be an eddy current. Sensor unit 30 may be embodied in an eddy current coil unit. Such an eddy current coil unit is known to those skilled in the art of sensor unit design and is therefore not illustrated in detail in FIG. 1.

A bias member 38 may be located between a shoulder portion 33 of sensor carrier 32 and a stop 35 associated with positioning frame 20. Stop 35 may be, by way of example and not by way of limitation, integrally formed within well 26, affixed within well 26 or otherwise substantially immovably located to provide a stop for bias member 38. Bias member 38 may be oriented to urge sensor carrier 32 toward an at-rest orientation. In the exemplary embodiment illustrated in FIG. 1, bias member 38 may be understood to be embodied in a helical compression spring urging sensor carrier 32 upward in FIG. 1 to reduce the extension "e" by sensor unit 30 beyond positioning frame 20.

Moving unit 22 may be embodied, by way of example and not by way of limitation, in a depth gauge or a micrometer unit. Moving unit 22 may be advanced within well 26 against a bias force provided by bias unit 38 to effect advancing sensor carrier 32 substantially along axis 27 in a manner to increase extension "e" by sensor unit 30. Details regarding interaction among positioning unit 22, sensor unit 30 and a multi-layer structure are described in further detail in connection with FIG. 2.

Figure 2:
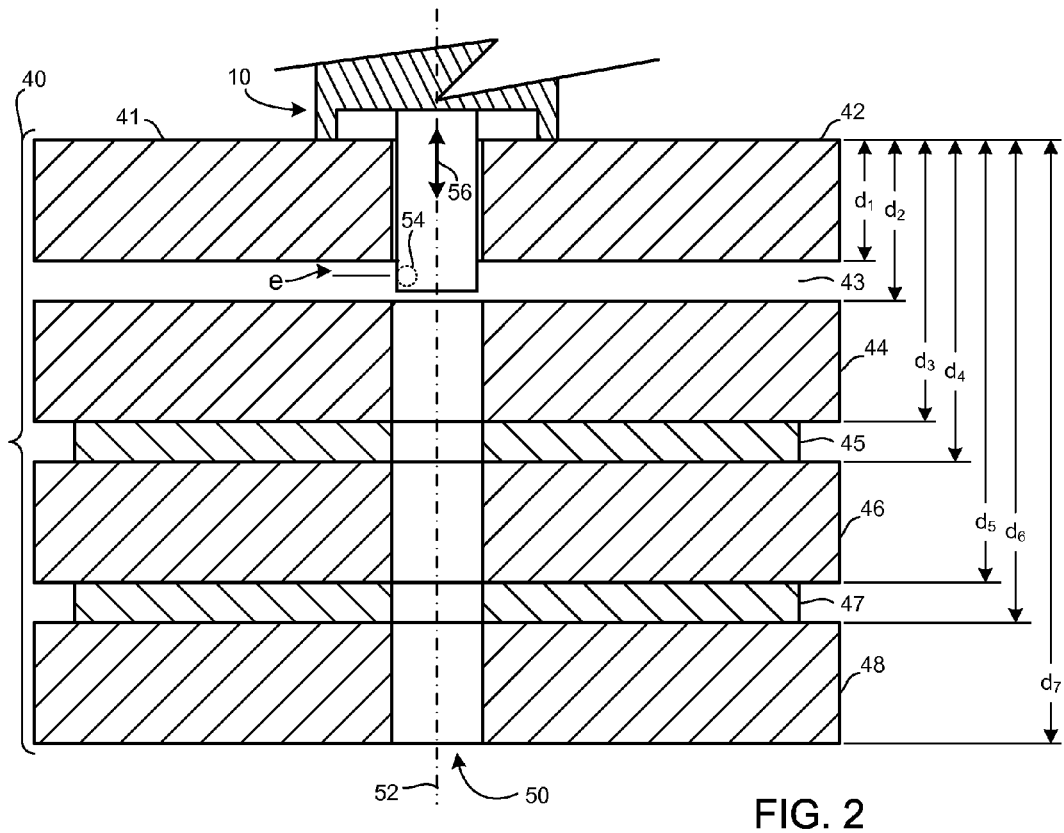
FIG. 2 is a schematic diagram illustrating employment of the present disclosure to evaluate layers of a multi-layer structure.

FIG. 2 is a schematic diagram illustrating employment of the present disclosure to evaluate layers of a multi-layer structure. In FIG. 2, an apparatus 10 configured generally as described in connection with FIG. 1 is illustrated in an installed orientation for evaluating a multi-layer structure 40.

Multi-layer structure 40 may include a first layer 42 extending a depth $d_1$ from a top surface 41. A second layer 44 may extend between a distance $d_2$ and a distance $d_3$ from top surface 41. A third layer 46 may extend between a distance $d_4$ and a distance $d_5$ from top surface 41. A fourth layer 48 may extend between a distance $d_6$ and a distance $d_7$ from top surface 41.

Layers 42, 44 may establish a gap 43 between distance $d_1$ and distance $d_2$ from top surface 41. Layers 44, 46 may establish an interlayer 45 between distance $d_3$ and distance $d_4$ from top surface 41. Layers 46, 48 may establish an interlayer 47 between distance $d_5$ and distance $d_6$ from top surface 41. Interlayers 45, 47 may be embodied in different materials than adjacent layers 44, 46, 48. Interlayers 45, 47 and layers 44, 46, 48 may each be embodied in a different material.

Multi-layer structure 40 may present an aperture 50 substantially oriented about an axis 52. Layers 44, 46, 48 may thus present a plurality of edges generally aligned athwart axis 52. The plurality of edges may be substantially in register crossingly arranged with respect to axis 52.

To carry out an evaluation of multi-layer structure 40 a user may advance the moving unit associated with apparatus 10 (not visible in FIG. 2; see moving unit 22, FIG. 1) to move sensor unit 54 generally parallel with axis 52 in directions indicated by arrows 56 to vary extension e from layer 42.

As sensor unit 54 may be moved to traverse multi-layer structure 40, sensor unit 54 may be oriented adjacent to differing materials exhibiting differing characteristics sensed by sensor unit 54. By way of example and not by way of limitation, sensor unit 54 may be configured to cooperate with a control unit (not visible in FIG. 2; see control unit 16, FIG. 1) to measure differences in impedance. This arrangement may be effected by configuring sensor unit 54 substantially as a type of a Wheatstone bridge with at least one portion of the bridge adjacent to the materials being evaluated. A Wheatstone bridge may be employed to measure an unknown electrical resistance or impedance by balancing two portions or legs of a bridge circuit, one portion of which includes the unknown impedance. Details of such a Wheatstone bridge are not described here but are within the understanding of one skilled in the art of sensor design.

As sensor unit 54 traverses multi-layer structure 40 via aperture 50, a change in impedance may be sensed by sensor unit 54 as sensor unit 54 passes each of layers 42, 44, 46, 48, gap 43 and interlayers 45, 47. By noting the depth to which apparatus 10 extends sensor unit 54 into aperture 50 as impedance sensed by sensor unit 54 varies, one may ascertain the thickness of each layer 42, 44, 46, 48, gap 43 and each interlayer 45, 47.

Sensor unit 54 may be configured for sensing another parameter than impedance such as, by way of further example and not by way of limitation, magnetic flux or capacitance. The size such as, by way of example and not by way of limitation, cross-section of sensor unit 54 taken along a plane substantially parallel with axis 52 may affect the resolution of changes that may be determinable by sensor unit 54. It may be that a smaller cross-section may permit finer discrimination of locations where changes in a measured parameter may occur, such as a transition from a material in a layer 44 to an air gap 43 as at distance $d_1$ from upper surface 41.

One skilled in the art of sensor design may also understand that apparatus 10 may operate substantially as described in connection with FIG. 2 in a situation where an exposed edge of multi-layer structure 40 is presented for evaluation rather than the interior surrounding edge of an aperture traversing multi-layer structure 40.

Figure 3:
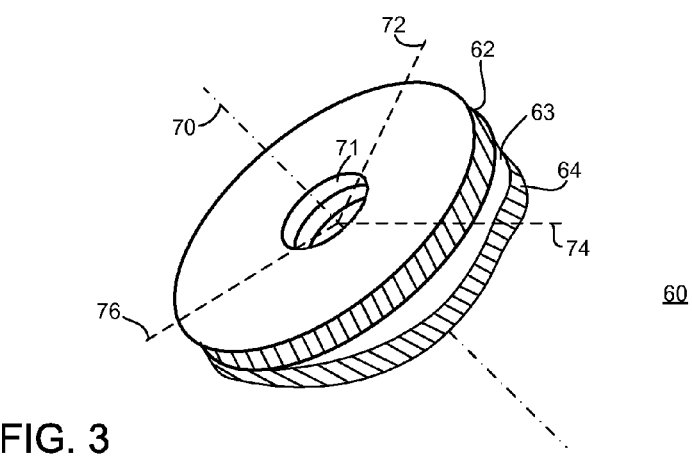
FIG. 3 is a schematic diagram illustrating employment of the present disclosure to evaluate layers of a multi-layer structure at different clock positions around an aperture.

FIG. 3 is a schematic diagram illustrating employment of the present disclosure to evaluate layers of a multi-layer structure at different clock positions around an aperture. In FIG. 3, a multi-layer structure 60 may include material layers 62, 64 separated by an air gap 63. An aperture 71 substantially symmetrical about an axis 72 may traverse multi-layer structure 60.

An apparatus configured substantially similarly to apparatus 10 (not shown in FIG. 3; see FIGS. 1 and 2) may be installed in an aperture 71 in a manner similar to the installation illustrated in FIG. 2 with respect to aperture 50. A series of evaluations may be performed by the inserted apparatus 10 generally as described in connection with FIG. 2. However, more than one series of evaluations may be performed in order to gain a more thorough evaluation of the extent of air gap 62. Such a more thorough evaluation maybe carried out by performing a series of evaluative readings of an electrical parameter, such as impedance, at several positions around the perimeter of aperture 71. By way of example and not by way of limitation, one may perform a series of evaluative readings at a twelve o'clock position 72. After completing evaluations at twelve o'clock position 72, apparatus 10 may be rotated to permit performance of a series of evaluative readings at another clock position, such as at three o'clock position 74. Alternatively, a portion of apparatus 10 such as moving unit 22 or sensing unit 12 may be rotated to permit evaluation at three o'clock position 74. After completing evaluations at three o'clock position 74, apparatus 10 may be rotated to permit performance of a series of evaluative readings at another clock position, such as at eight o'clock position 76. Performing such a series of evaluations at different clock positions about aperture 71 may permit one to ascertain whether separation of air gap 63 from layers 62, 64 is not uniform about aperture 71, as is the case illustrated in FIG. 3.

Figure 4:
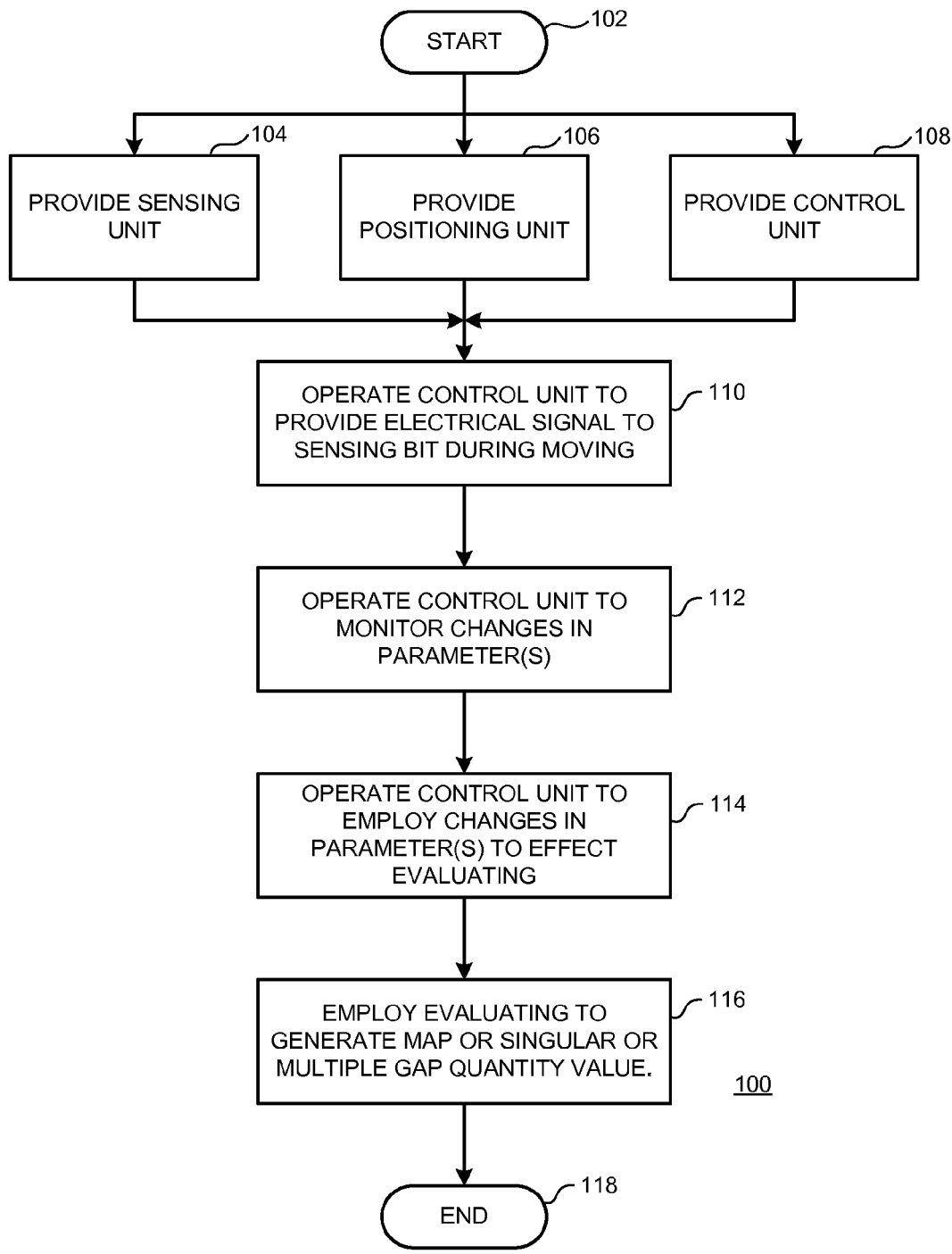
FIG. 4 is a flow diagram illustrating the method of the present disclosure.

FIG. 4 is a flow diagram illustrating the method of the present disclosure. In FIG. 4, a method 100 for evaluating interlayer gaps in a multi-layer structure to generate a map representing said evaluating begins at a START locus 102. The multi-layer structure presents a plurality of edges generally aligned athwart an axis.

Method 100 continues with, in no particular order: (1) providing a sensing unit configured for sensing at least one parameter, as indicated by a block 104; (2) providing a positioning unit coupled with the sensing unit, as indicated by a block 106; the positioning unit may be configured to effect moving the sensing unit generally parallel with the axis; and (3) providing a control unit coupled with at least one of the positioning unit and the sensing unit, as indicated by a block 108.

Method 100 continues with operating the control unit to provide an electrical signal to the sensing unit, as indicated by a block 110. Alternatively, the electrical signal may be provided to the sensing unit during the moving of the sensing unit.

Method 100 continues with operating the control unit to monitor changes in the at least one parameter as the sensing unit moves past the plurality of edges, as indicated by a block 112.

Method 100 continues with operating the control unit to employ the changes in the at least one parameter to effect the evaluating, as indicated by a block 114.

Method 100 continues with employing the evaluating to generate the map, as indicated by a block 116. The map may be in the form of a graphic display, a tabular representation of a graphic display or another format useful to a user. The map may be stored in a storage unit for later use or evaluation.

Method 100 terminates at an END locus 118.

It is to be understood that, while the detailed drawings and specific examples given describe preferred embodiments of the disclosure, they are for the purpose of illustration only, that the apparatus and method of the disclosure are not limited to the precise details and conditions disclosed and that various changes may be made therein without departing from the spirit of the disclosure which is defined by the following claims:

What is claimed is:

1. An apparatus for evaluating interlayer gaps in a multi-layer structure; said multi-layer structure presenting a plurality of edges generally aligned athwart an axis and that surround an aperture traversing at least a portion of said multi-layer structure and generally parallel with said axis; said apparatus comprising:

(a) a sensing unit configured for sensing at least one parameter;

(b) a positioning unit coupled with said sensing unit; said positioning unit comprising a positioning frame selectively coupled to said multi-layer structure such that said positioning frame substantially circumscribes said aperture when coupled to said multi-layer structure and such that said sensing unit is aligned substantially coaxially with said axis, said positioning unit being configured to effect moving said sensing unit generally along said axis through said aperture with a clearance between said sensor unit and said multi-layer structure, and configured to effect rotation of said sensing unit about said axis; and (c) a control unit coupled with at least one of said positioning unit and said sensing unit;

said control unit providing an electrical signal to said sensing unit; said control unit monitoring changes in said at least one parameter as said sensing unit moves past said plurality of edges and rotates within said aperture; said control unit employing said changes in said at least one parameter to effect said evaluating of a distance between adjacent layers of said multi-layer structure and a thickness of layers of said multi-layer structure.

2. The apparatus for evaluating interlayer gaps in a multi-layer structure as recited in claim 1 wherein said positioning unit is configured to indicate displacement of said sensing unit by said positioning unit; said displacement being employed by said control unit in said evaluating.

3. The apparatus for evaluating interlayer gaps in a multi-layer structure as recited in claim 1 wherein said positioning unit is embodied in a micrometer unit.

4. The apparatus for evaluating interlayer gaps in a multi-layer structure as recited in claim 1 wherein said sensing unit includes an eddy current coil unit.

5. The apparatus for evaluating interlayer gaps in a multi-layer structure as recited in claim 4 wherein said at least one parameter is impedance experienced by said eddy current coil unit.

6. The apparatus for evaluating interlayer gaps in a multi-layer structure as recited in claim 1 wherein said positioning unit is configured to indicate displacement of said sensing unit by said positioning unit; said displacement being employed by said control unit in said evaluating.

7. The apparatus for evaluating interlayer gaps in a multi-layer structure as recited in claim 6 wherein said sensing unit includes an eddy current coil unit.

8. The apparatus for evaluating interlayer gaps in a multi-layer structure as recited in claim 7 wherein said at least one parameter is impedance experienced by said eddy current coil unit.

9. A system for determining thicknesses of differing material layers generally along an axis in a multi-layer structure; said thicknesses being bound by a plurality of edges substantially in register crossingly arranged with respect to said axis and that substantially surround an aperture traversing at least a portion of said multi-layer structure and generally parallel with said axis; the system comprising:

(a) an electromagnetic sensor unit configured for sensing at least one electromagnetic parameter;

(b) a positioning unit coupled with said sensor unit; said positioning unit comprising a positioning frame selectively coupled to said multi-layer structure such that said positioning frame substantially circumscribes said aperture when coupled to said multi-layer structure and such that said electromagnetic sensor unit is aligned substantially coaxially with said axis, said positioning unit effecting movement of said sensor unit generally along said axis through said aperture with a clearance between said sensor unit and said multi-layer structure, and effecting rotation of said sensor unit about said axis; and (c) a monitoring unit coupled with at least one of said sensor unit and said positioning unit; said monitoring unit providing an electrical input signal to said sensor unit and receiving indications of changes in said at least one electromagnetic parameter from said sensor unit as said sensor unit moves along said axis past said plurality of edges and rotates within said aperture; said monitoring unit employing said changes in said at least one electromagnetic parameter to effect said determining of a distance between adjacent differing material layers of said multi-layer structure and the thicknesses of the differing material layers of said multi-layer structure.

10. The system for determining thicknesses of differing material layers generally along an axis in a multi-layer structure as recited in claim 9 wherein said positioning unit is configured to indicate displacement of said sensor unit by said positioning unit; said displacement being employed by said monitoring unit in said determining.

11. The system for determining thicknesses of differing material layers generally along an axis in a multi-layer structure as recited in claim 10 wherein said positioning unit is embodied in a micrometer unit.

12. The system for determining thicknesses of differing material layers generally along an axis in a multi-layer structure as recited in claim 11 wherein said sensor unit includes an eddy current coil unit.

13. The system for determining thicknesses of differing material layers generally along an axis in a multi-layer structure as recited in claim 12 wherein said at least one electromagnetic parameter is impedance experienced by said eddy current coil unit.

14. A method for evaluating interlayer gaps in a multi-layer structure to generate a map representing said evaluating; said multi-layer structure presenting a plurality of edges generally aligned athwart an axis and that substantially surround an aperture traversing at least a portion of said multi-layer structure and generally parallel with said axis; the method comprising:

(a) in no particular order:
(1) providing a sensing unit configured for sensing at least one parameter;
(2) providing a positioning unit coupled with said sensing unit;
(a) selectively coupling a positioning frame of said positioning unit to said multi-layer structure such that said positioning frame substantially circumscribes said aperture and such that said sensing unit is aligned substantially coaxially with said axis, said positioning unit being configured to effect moving said sensing unit generally parallel with said axis through said aperture with a clearance between said sensor unit and said multi-layer structure, and configured to effect rotation of said sensing unit about said axis; and
(3) providing a control unit coupled with at least one of said positioning unit and said sensing unit;

(b) operating said control unit to provide an electrical signal to said sensing unit;

(c) operating said control unit to monitor changes in said at least one parameter as said sensing unit moves past said plurality of edges and rotates within said aperture;

(d) operating said control unit to employ said changes in said at least one parameter to effect said evaluating of a distance between adjacent layers of said multi-layer structure and a thickness of the layers of said multi-layer structure; and (e) employing said evaluating to generate said map.

15. The method for evaluating interlayer gaps in a multi-layer structure as recited in claim 14 wherein said positioning unit is a micrometer unit arranged to indicate displacement of said sensing unit by said positioning unit; said displacement being employed by said control unit in said evaluating.

16. The method for evaluating interlayer gaps in a multi-layer structure as recited in claim 15 wherein said sensing unit includes an eddy current coil unit.

17. The method for evaluating interlayer gaps in a multi-layer structure as recited in claim 16 wherein said at least one parameter is impedance experienced by said eddy current coil unit.

* * * * *